United States Patent [19]

Mayer, deceased et al.

[11] 4,366,231
[45] Dec. 28, 1982

[54] PHOTOGRAPHIC MATERIAL CONTAINING A STABILIZER, A PROCESS FOR ITS PRODUCTION, A DEVELOPMENT PROCESS, NEW PYRAZOLES, A PROCESS FOR THEIR PRODUCTION AND INTERMEDIATE PRODUCTS

[75] Inventors: Karl H. Mayer, deceased, late of Leverkusen, Fed. Rep. of Germany, by Hildegard E. Mayer, Annedore Mayer, Andrea Mayer, heirs; Klaus Sasse, Bergisch Gladbach; Anita von König, Krefeld, both of Fed. Rep. of Germany

[73] Assignee: Agfa Gevaert Aktiengesellschaft, Leverkusen, Fed. Rep. of Germany

[21] Appl. No.: 223,746

[22] Filed: Jan. 9, 1981

[30] Foreign Application Priority Data

Jan. 17, 1980 [DE] Fed. Rep. of Germany ....... 3001498

[51] Int. Cl.$^3$ ............................................. G03C 1/34
[52] U.S. Cl. .................................... 430/375; 430/615; 430/614; 430/446; 544/251; 430/448; 430/551; 430/510
[58] Field of Search ............... 430/615, 614, 446, 551, 430/448, 510, 375

[56] References Cited

U.S. PATENT DOCUMENTS 2,743,181  4/1956  Allen et al. ......................... 430/615
3,244,521  4/1966  Dersch et al. ...................... 430/615

Primary Examiner—Won H. Louie, Jr.
Attorney, Agent, or Firm—Connolly and Hutz

[57] ABSTRACT

Pyrazoles of the formula

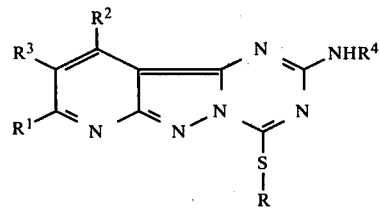

are useful as stabilisers in photographic materials.

7 Claims, No Drawings

PHOTOGRAPHIC MATERIAL CONTAINING A STABILIZER, A PROCESS FOR ITS PRODUCTION, A DEVELOPMENT PROCESS, NEW PYRAZOLES, A PROCESS FOR THEIR PRODUCTION AND INTERMEDIATE PRODUCTS

This invention relates to a photographic material containing at least one silver halide emulsion layer which incorporates stabilisers capable of protecting the photographic material against the formation of fog, colour fog and contact fog on silver layers containing colloidal silver.

The invention also relates to a development process, to a process for the production of a photographic material, to new pyrazoles, to a process for their production and to new intermediate products.

It is known that materials containing photosensitive silver halide emulsions, particularly chemically sensitised silver halide emulsions, have a tendency to form fogs, produced by nuclei which can be developed without exposure. Fogging such as this occurs in particular in the event of prolonged storage, particularly under conditions of high temperature and humidity, in the event of prolonged development or in the event of development at excessively high temperatures, through certain additives and in the case of heavily ripened emulsions.

Colour photographic films may, for various purposes, comprise filter layers containing colloidal silver which are arranged adjacent to the individual photosensitive emulsion layers. Thus, the auxiliary layer between the blue-sensitive and the green-sensitive silver halide layers may contain yellow colloidal silver. The function of this yellow filter layer is to keep the fraction of unwanted blue light away from the red-sensitive and green-sensitive emulsion layers. This layer acting as an anti-halation layer between the support layer and the immediately adjacent silver halide layer may consist of black, brown or blue colloidal silver. Coloured colloidal silver may also be incorporated in an overcoating layer to correct colour reproduction.

These various layers containing colloidal silver frequently have an adverse effect upon the adjoining emulsion layers, particularly when the colour materials in question are treated with developers containing complex formers for the silver halide present in the emulsion layers, such as alkali metal thiocyanate, amine compounds or relatively large quantities of sulphite and alkali metal halides. Under the effect of these complex formers, physical development may take place on the nuclei of colloidal silver present in the auxiliary layers. The result of this is that, in the case of colour negative materials, colour fogging and, in the case of colour reversal materials, the amount of fogging silver in the first developer is increased so that, during subsequent colour development, colour density is correspondingly reduced. These unfavourable phenomena are known collectively as contact fogging. Conventional measures for preventing contact fogging are attended by various disadvantages. Thus, the incorporation of gelatin-containing separation layers between the layer containing colloidal silver and the photosensitive silver halide emulsion layers does not completely prevent contact fogging and is attended by the disadvantage of a reduction in image definition. The reduction of contact fogging by the addition of heterocyclic mercaptans to silver dispersions, as described in German Offenlegungsschrift No. 2,336,721, can change the colour of the silver dispersion, as described for example by F. Evva in J. Signal AM 6, 25 (1978). Any change in the colour of the silver filter yellow produces a reduction in the sensitivity of the underlying emulsion layers.

In addition, it is in practice possible for development to occur in the presence of thiosulphates, for example through the entrainment of developer substances into the fixing bath or into the bleach fixing bath, particularly in high-speed processing where there is no stop bath between the developer and fixing or bleach-fixing bath, and through the entrainment of sodium thiosulphate into the developer, for example by clips and other components of the apparatus. This gives rise to heavy fogging in standard photographic materials, particularly during processing at high temperatures.

It is known that so-called anti-fogging agents or stabilisers may be added to photographic silver halide emulsions to reduce this fogging. A stabilising effect such as this is developed, for example, by heterocyclic mercapto compounds, for example of the type described in German Offenlegungsschrift No. 1,962,605, U.S. Pat. No. 3,695,881 and German Offenlegungsschrift No. 2,336,721. However, these stabilisers have the disadvantage that, in effective concentrations, they are capable of reducing the sensitivity of the stabilised emulsion, thus impairing its effectiveness. The gradation of the emulsion can also be adversely affected by these stabilisers.

Stabilisers have to satisfy a variety of requirements, particularly with regard to their interaction with other photographic additives and in view of the multiplicity of photographic reproduction processes and the photographic materials used therein. Known stabilisers do not always satisfy these requirements.

Accordingly, there is still a need for stabilisers which stabilise photographic materials against fogging, colour fogging and flattening of gradation.

An object of the present invention is to provide stabilisers which are capable of stabilising photographic materials against fogging, colour fogging and contact fogging on silver layers containing colloidal silver. A further object of the invention is to provide photographic materials containing at least one silver halide emulsion layer which are stabilised with these compounds.

The present invention therefore provides:

(1) a photographic material consisting of a support layer and, applied thereto, at least one light sensitive silver halide emulsion layer and, optionally, further layers, at least one layer containing a compound corresponding to formula (I) below:

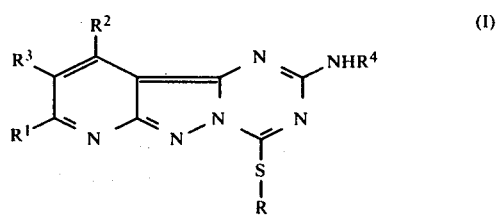

in which:

R represents alkyl, alkenyl, aryl, aralkyl or cycloalkyl;

R$^1$, R$^2$ and R$^3$, which may be the same or different, represent hydrogen, alkyl, aryl, cycloalkyl or aralkyl;

R$^4$ represents hydrogen or —COR$^5$;

R$^5$ represents alkyl, aryl, cycloalkyl, aralkyl or —OR$^6$ and

R$^6$ represents alkyl, aryl, cycloalkyl, aralkyl.

The present invention also provides:

(2) a process for the production of a photographic material containing at least one silver halide emulsion layer by precipitating the silver halide in the presence of a protective colloid, optionally physically and chemically ripening the silver halide and applying the casting solution obtained to a support layer, characterised in that a compound corresponding to formula (I) below:

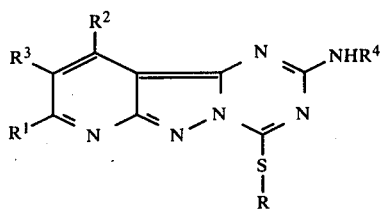

(I)

in which

R represents alkyl, alkenyl, aryl, aralkyl or cycloalkyl;

R$^1$, R$^2$ and R$^3$ which may be the same or different, represent hydrogen, alkyl, aryl, cycloalkyl or aralkyl;

R$^4$ represents hydrogen or —COR$^5$;

R$^5$ represents alkyl, aryl, cycloalkyl, aralkyl or —OR$^6$ and

R$^6$ represents alkyl, aryl, cycloalkyl, aralkyl, is added, at the latest to the casting solution.

In addition, there has been found:

(3) a process for the development of photographic materials comprising a support layer and at least one light sensitive silver halide emulsion layer in the presence of a compound corresponding to formula (I).

The present invention also provides (4) new 2-aminopyrido-[2,3-d]-[1,3,5]-triazino-[1,2-b]-pyrazoles corresponding to general formula (I) below:

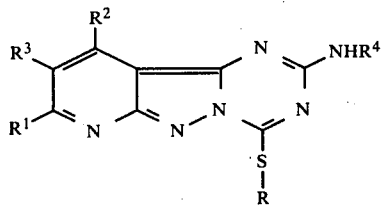

(I)

in which

R represents alkyl, alkenyl, aryl, aralkyl or cycloalkyl;

R$^1$, R$^2$ and R$^3$ which may be the same or different, represent hydrogen, alkyl, aryl, cycloalkyl or aralkyl;

R$^4$ represents hydrogen or —COR$^5$;

R$^5$ represents alkyl, aryl, cycloalkyl, aralkyl or —OR$^6$ and

R$^6$ represents alkyl, aryl, cycloalkyl, aralkyl.

The present invention also provides (5) a process for producing a pyrazole corresponding to formula (I) by reacting a 3-aminopyrazolo-[3,4-b]-pyridine corresponding to the following tautomeric formulae (IIa) and (IIb)

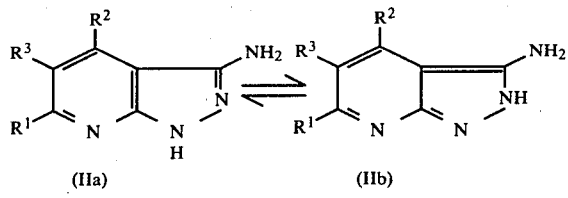

in which

R$^1$, R$^2$ and R$^3$ are as defined above, with an N-cyanimido-dithiocarbonic acid ester corresponding to the following formula

(III)

in which

R is as defined above, in the presence of an inert organic solution promoter, particularly at a temperature in the range of from 50° to 250° C., and optionally acylating the product of this reaction with a compound containing the group —COR$^5$ in which R$^5$ is as defined above.

Preferred acylating agents containing the group —COR$^5$ are chloroformic acid esters, particularly ClCOOR$^6$, acyl chlorides, particularly ClCOR$^5$ and pyrocarbonic acid esters.

In preferred embodiments, R represents an alkyl or alkenyl radical containing from 1 to 6 carbon atoms, an aralkyl radical containing up to 10 carbon atoms and, in particular, an alkyl or alkenyl radical containing from 1 to 4 carbon atoms or an aralkyl radical containing from 1 to 2 carbon atoms in the alkyl moiety and phenyl in the aryl moiety. Examples of such radicals include methyl, ethyl, n- and i-propyl, n- and i-butyl, n-hexyl, allyl, benzyl and phenyl ethyl.

The substituents R$^1$, R$^2$ and R$^3$ preferably represent hydrogen, phenyl, alkyl containing from 1 to 4 carbon atoms and preferably from 1 to 2 carbon atoms. Methyl, ethyl, n- and i-propyl, n- and i-butyl are particularly preferred.

The substituent R$^4$ is preferably hydrogen or the radical COR$^5$ where R$^5$ represents C$_1$-C$_3$-alkyl, particularly methyl, or a C$_1$-C$_6$-alkoxy or cycloalkoxy radical, particularly the radical —O—C$_2$H$_5$.

In a particularly preferred embodiment, R$^1$, R$^2$ and, in particular, R$^3$ represent hydrogen.

The substituents R, R$^1$, R$^2$ and R$^3$ are understood to be substituents of the type which may in turn be substituted, particularly by substituents of the type commonly encountered in compounds used photographically.

It has also been found that the reaction of the 3-aminopyrazolo-[3,4-b]-pyridines corresponding to formulae (IIa) and (IIb) with the N-cyanimidodithiocarbonic acid esters corresponding to formula (III) to form the 2-aminopyrido-[2,3-d]-[1,3,5-]-triazino-[1,2-b]-pyrazoles corresponding to formula (I) takes place via the intermediate stage (IV) which may be interrupted, providing that the reaction is carried out suitably or may optionally be isolated from the mother liquor accumulating during production of the compounds of formula I:

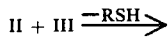

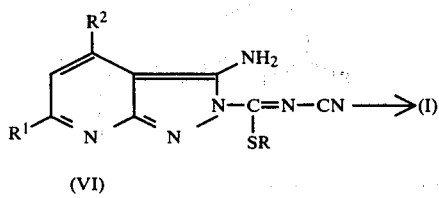

The following reaction scheme shows examples of reactions of individual reactants suitable for use in accordance with the invention, the 3-aminopyrazolo-/3,4-b/pyridines each being shown only in the taumeric formulation corresponding to (IIB) for simplicity:

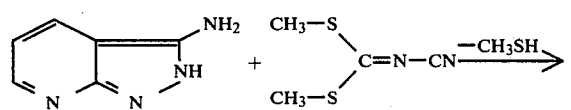

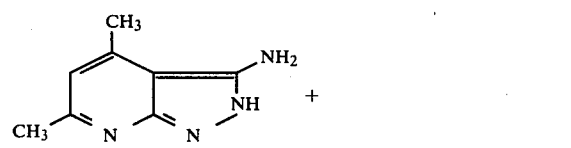

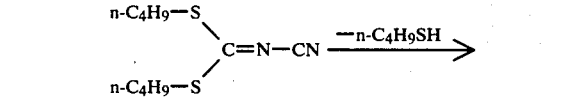

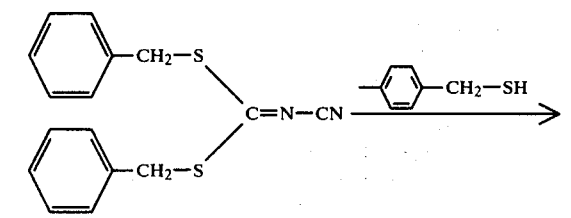

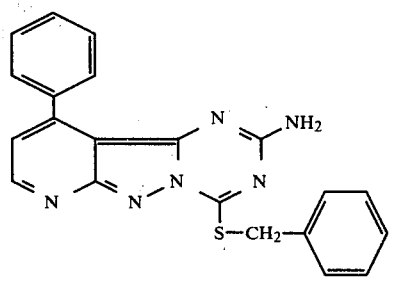

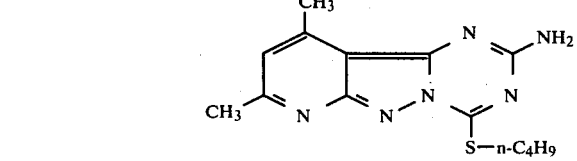

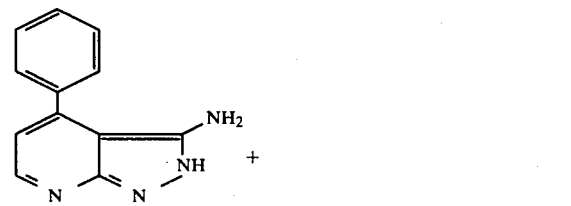

The 3-aminopyrazolo-[3,4-b]-pyridines corresponding to tautomeric formulae (IIa) and (IIb) which are used as starting materials are known or may be obtained by known process as described in German Offenlegungsschrifts Nos. 2,160,780; 2,238,400 and 2,355,967 and Croat.Chem.Acta 47 (1975), 127.

The following are specific examples of suitable starting pyridines: 3-aminopyrazolo-[3,4-b]-pyridine; 3-amino-4-methyl-[3,4-b]-pyridine; 3-amino-4-ethyl-[3,4-b]-pyridine; 3-amino-4-i-propyl-[3,4-b]-pyridine; 3-amino-4-n-butyl-[3,4-b]-pyridine; 3-amino-4-phenyl-[3,4-b]-pyridine; 3-amino-6-methyl-[3,4-b]-pyridine; 3-amino-6-ethyl-[3,4-b]-pyridine; 3-amino-6-n-propyl-[3,4-b]-pyridine; 3-amino-6-i-butyl-[3,4-b]-pyridine; 3-amino-6-phenyl-[3,4-b]-pyridine; 3-amino-4,6-dimethyl-[3,4-b]-pyridine; 3-amino-4,6-diethyl-[3,4-b]-pyridine; 3-amino-4-methyl-6-ethyl-[3,4-b]-pyridine; 3-amino-4-ethyl-6-methyl-[3,4-b]-pyridine; 3-amino-4-methyl-6-phenyl-[3,4-b]-pyridine; 3-amino-4-phenyl-6-methyl-[3,4-b]-pyridine and 3-amino-4,6-diphenyl-[3,4-b]-pyridine.

The N-cyanimido-dithiocarbonic acid esters of formula (III) used as starting materials are known or may be obtained by known processes such as are described in Liebigs Ann.Chem. 331 (1904), 265; J.org.Chem. 32 (1967), 1566 and 2567, Tetrahedron Letters (1966), 1885 and U.S. Pat. Nos. 3,299,129 and 3,658,901.

Examples of suitable N-cyanimido-dithiocarbonic acid esters are
N-cyanimido-dithiocarbonic acid methyl ester;

N-cyanimido-dithiocarbonic acid ethyl ester;
N-cyanimido-dithiocarbonic acid n-propyl ester;
N-cyanimido-dithiocarbonic acid i-propyl ester;
N-cyanimido-dithiocarbonic acid n-butyl ester;
N-cyanimido-dithiocarbonic acid i-butyl ester;
N-cyanimido-dithiocarbonic acid allyl ester;
N-cyanimido-dithiocarbonic acid benzyl ester and
N-cyanimido-dithiocarbonic acid phenylethyl ester.

Suitable solution promoters are any organic solvents which are inert to the particular reactants used. Preferred organic solvents of this type are aliphatic alcohols, such as methanol, ethanol, isopropanol or butanol; ethers such as tetrahydrofuran, dioxane, ethylene glycol monoethyl ether or ethylene glycol diethyl ether; glycols such as ethylene glycol, propylene glycol or diethylene glycol and corresponding ethers with aliphatic alcohols, such as diethylene glycol dimethyl ether; hydrocarbons such as ligroin, toluene, xylene or tetralin; halogenated hydrocarbons such as chloroform, carbon tetrachloride, chlorobenzene or dichlorobenzenes; nitriles, such as acetonitrile or, propionitrile; carboxylic acid amides, such as dimethyl formamide or dimethyl acetamide and heterocyclic bases, such as pyridine, picolines, collidines, quinoline or isoquinoline. Standard commercially available mixtures of these solvents can also be used.

The reaction may be carried out both under normal pressure and under elevated pressure.

The reaction temperatures may be varied over a relatively wide range. In general, the reaction is carried out at temperatures in the range from 50° to 250° C., preferably at temperatures in the range from 50° to 150° C. and, more particularly, at temperatures in the range from 80° to 120° C.

In the practical application of the process according to the invention, at least 1 mole of the N-cyanimido-dithiocarbonic acid ester of formula (III) is generally used per mole of the 3-aminopyrazolo-[3,4-b]-pyridine corresponding to formula (II).

In the course of the reaction according to the invention, the starting materials generally enter completely or partly into solution, whilst the final products crystallise out. The final products may be separated off by cooling and/or by the addition of precipitants, such as water, lower aliphatic ethers, such as diethyl ether or dibutyl ether, or lower aliphatic hydrocarbons, such as petroleum ether or light petrol.

The compounds listed in Table 1 below are examples of the compounds corresponding to formula (I):

TABLE 1

| No. | R | $R^1$ | $R^2$ | $R^4$ |
|---|---|---|---|---|
| 1.1 | methyl | H | H | H |
| 1.2 | ethyl | H | H | H |
| 1.3 | n-propyl | H | H | H |
| 1.4 | i-propyl | H | H | H |
| 1.5 | n-butyl | H | H | H |
| 1.6 | i-butyl | H | H | H |
| 1.7 | allyl | H | H | H |
| 1.8 | benzyl | H | H | H |
| 1.9 | phenylethyl | H | H | H |
| 1.10 | n-pentyl | H | H | H |
| 1.11 | n-hexyl | H | H | H |
| 1.12 | methyl | methyl | H | H |
| 1.13 | ethyl | methyl | H | H |
| 1.14 | propyl | methyl | H | H |
| 1.15 | isopropyl | methyl | H | H |
| 1.16 | allyl | methyl | H | H |
| 1.17 | butyl | methyl | H | H |
| 1.18 | i-butyl | methyl | H | H |
| 1.19 | sec.-butyl | methyl | H | H |
| 1.20 | pentyl | methyl | H | H |
| 1.21 | hexyl | methyl | H | H |
| 1.22 | benzyl | methyl | H | H |
| 1.23 | methyl | H | methyl | H |
| 1.24 | methyl | methyl | methyl | H |
| 1.25 | methyl | phenyl | H | H |
| 1.26 | methyl | H | phenyl | H |
| 1.27 | methyl | methyl | phenyl | H |
| 1.28 | methyl | phenyl | methyl | H |
| 1.29 | methyl | phenyl | phenyl | H |
| 1.30 | methyl | ethyl | ethyl | H |
| 1.31 | ethyl | methyl | methyl | H |
| 1.32 | n-propyl | methyl | methyl | H |
| 1.33 | i-propyl | methyl | methyl | H |
| 1.34 | n-butyl | methyl | methyl | H |
| 1.35 | i-butyl | methyl | methyl | H |
| 1.36 | n-pentyl | methyl | methyl | H |
| 1.37 | n-hexyl | methyl | methyl | H |
| 1.38 | allyl | methyl | methyl | H |
| 1.39 | benzyl | methyl | methyl | H |
| 1.40 | phenylethyl | methyl | methyl | H |
| 1.41 | n-butyl | ethyl | ethyl | H |
| 1.42 | benzyl | n-butyl | n-butyl | H |
| 1.43 | methyl | methyl | methyl | $COOC_2H_5$ |

The production of some of these compounds is described by way of example in the following:

Compound 1.24

81 g (0.5 mole) of 3-amino-4,6-dimethylpyrazolo-[3,4-b]-pyridine and 146 g (1 mole) of N-cyanimido-dithiocarbonic acid methyl ester are heated under reflux for 25 hours in 1500 ml of pyridine. A clear solution is formed with continuous elimination of methyl mercaptan, being filtered in the presence of active carbon and concentrated by evaporation to dryness in a water jet vacuum using a rotary evaporator. Recrystallisation of the residue from glycol monomethyl ether gives 2-amino-4-methylmercapto 7,9-dimethyl-pyrido-[2,3-d]-[1,3,5]-triazino-[1,2-b]-pyrazole in the form of yellow crystals. Yield: 50 to 60 g, melting point: 306° to 307° C.

The compound can occur in four different crystal forms which give different IR-spectra. The $^1$H-NMR and MS-spectra are identical.

Concentration of the glycol monomethyl ether mother liquor by evaporation gives a crystalline residue from which 2-(methyl-mercapto-N-cyanimidocarbonyl)-3-amino-4,6-dimethylpyrazolo-[3,4-b]-pyridine may be isolated in the form of yellow crystals after stirring with dimethyl formamide, filtration under suction and recrystallisation from glycol monomethyl ether. This compound corresponds to the following formula:

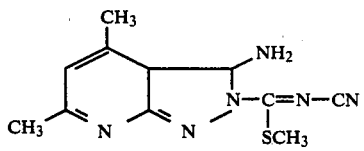

and is clearly an intermediate product in the preparation in accordance with the invention of compounds corresponding to formula (I). Yield: 5 to 10 g, melting point: 212° C.

Compound 1.39

32.4 g (0.2 mole) of 3-amino-4,6-dimethylpyrazolo-[3,4-b]-pyridine and 59.6 g (0.2 mole) of N-cyanimido-dithiocarbonic acid benzyl ester are heated under reflux for 14 hours in 100 ml of pyridine. The solution is concentrated by evaporation, acetone is added to the residue which is then filtered under suction and washed with ethanol, giving 2-amino-4-benzylmercapto-7,9-dimethylpyrido-[2,3-d]-[1,3,5]-triazino-[1,2-b]-pyrazole in the form of yellow crystals. Yield: 15 g, melting point: 263° to 265° C.

Compound 1.12

14.8 g (0.1 mole) of 3-amino-6-methylpyrazolo-[3,4-b]-pyridine and 29.2 g (0.2 mole) of N-cyanimido-dithiocarbonic acid methyl ester are heated under reflux for 1.5 hours in 50 ml of pyridine. The starting materials pass into solution and, after a short time, 2-amino-4-methylmercapto-7-methylpyrido-[2,3-d]-[1,3,5]-triazino-[1,2-b]-pyrazole crystallises out in the form of yellow crystals. After cooling and filtration under suction, the crystals thus formed are washed with methanol and petroleum ether. Yield: 20 g, melting point: 283° to 284° C.

Compound 1.1

Following the procedure used to produce compound 1.12, 48 g of 2-amino-4-methylmercaptopyrido-[2,3-d]-[1,3,5]-triazino-[1,2-b]-pyrazole in the form of yellow crystals melting at 295° to 296° C. are obtained in 3 hours at reflux temperature from 31.7 g (0.24 mole) of 3-aminopyrazolo-[3,4-b]-pyridine and 69 g (0.47 mole) of N-cyanimido-dithiocarbonic acid methyl ester in 150 ml of pyridine.

Compound 1.17

148 g (1 mole) of 3-amino-6-methylpyrazolo-[3,4-b]-pyridine and 345 g (1.5 moles) of N-cyanimido-dithiocarbonic acid butyl ester are boiled for 7 hours in 500 ml of pyridine. The solvent and the butyl mercaptan formed are distilled off in a water jet vacuum, the residue is stirred with acetone, filtered under suction, washed with acetone and dissolved in and allowed to crystallise from toluene. After filtration under suction and washing with petroleum ether, 160 g of 2-amino-4-butylmercapto-7-methylpyrido-[2,3-b]-[1,3,5]-triazino-[1,2-b]-pyrazole are obtained in the form of yellow crystals melting at 191° to 192° C.

Compound 1.5

10.5 g (0.078 mole) of 3-aminopyrazolo-[3,4-b]-pyridine and 36 g (0.156 mole) of N-cyanimido-dithiocarbonic acid butyl ester are heated for 6 hours to 100° C. in 40 ml of pyridine. After about 1 hour, 2-amino-4-butylmercaptopyrido-[2,3-d]-[1,3,5]-triazino-[1,2-b]-pyrazole crystallises out. After cooling, approximately 100 ml of acetone are added, the yellow crystals are filtered off under suction and purified by dissolution in and crystallisation from methanol. Yield: 7 g, melting point: 197° to 198° C.

Compound 1.43

6.5 g (0.025 mole) of compound 1.17 are suspended in 500 ml of acetone and, following the addition of 10 ml of diethyl carbonate and 30 ml of a 0.25% sodium methylate solution, the mixture is stirred for several hours at 40° to 50° C. until the evolution of carbon dioxide is over. After cooling, any unreacted starting material is separated by filtration under suction and the filtrate is concentrated in vacuo. The residue is washed free from salts and then recrystallised from 75 ml of alcohol. Yield 1.5 g, decomposition point 298° C.

Analysis: calculated 25.3% N, observed 25.4% N.

Photographic emulsions or materials containing the stabilisers according to the invention may also contain other stabilisers such as, for example, homopolar or salt-like compounds of mercury with aromatic or heterocyclic rings. Suitable additional stabilisers are heterocyclic mercapto compounds, for example phenyl mercaptotetrazole, quaternary benzthiazole derivatives and benzotriazole.

In a preferred embodiment of the invention, the stabilisers according to the invention are used in combination with stabilisers of the indolizine type known per se, preferably in combination with tri- or tetra-azaindolizines and, more particularly, in combination with those which are substituted by at least one hydroxyl and/or amino group. Indolizines of this type are described for example in the article by Birr in Z. Wiss. Phot. 47 (1952), pages 2 to 58, and in U.S. Pat. No. 2,944,902.

Particularly preferred additional indolizine derivatives correspond to the following formula:

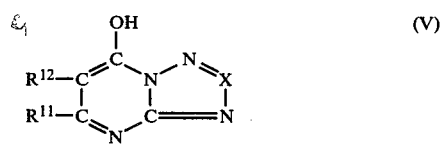

in which

X represents C-R$^{10}$ or N;

R$^{10}$ and R$^{11}$ which may be the same or different, represent a hydrogen atom, an alkyl group, a cycloalkyl, aralkyl or an aryl group and R$^{12}$ represents a hydrogen atom, an alkyl group, a carboxy group or an alkoxy carbonyl group.

In principle, additional stabilisers may be added to the photographic materials or emulsions before, after or at the times at which the stabilisers according to the invention are also added.

Particularly preferred additional stabilisers of the azaindene type are, in particular, those of the type listed in Table 2 below:

TABLE 2

| No. | Compound |
|---|---|
| 2.1 | 4-hydroxy-6-methyl-1,3,3a,7-tetraazaindene, |
| 2.2 | 4-hydroxy-5-carboxy-1,3,3a,7-tetraazaindene, |
| 2.3 | 4-hydroxy-5-carbethoxy-1,3,3a,7-tetraazaindene, |
| 2.4 | 2-β-hydroxyethyl-4-hydroxy-6-methyl-1,3,3a,7-tetraazaindene |
| 2.5 | 2-methyl-4-hydroxy-1,3,3a,7-tetraazaindene, |

TABLE 2-continued

| No. | Compound |
|---|---|
| 2.6 | 4-hydroxy-6-methyl-1,2,3,3a,7-pentaazaindene. |

The present invention is suitable for photographic materials containing silver halide emulsions of any type. These silver halide emulsions may contain as silver halide silver bromide, silver chloride or mixtures thereof, which may have a small silver iodide content of up to 10 mole percent.

The photographic materials may be developed with standard colour developer substances, for example N,N-dimethyl-p-phenylene diamine; 4-amino-3-methyl-N-ethyl-N-methoxy ethyl aniline; 2-amino-5-diethylamino-toluene; N-butyl-N-ω-sulphobutyl-p-phenylene diamine; 2-amino-5-(N-ethyl-N-β-methane-sulphonamido-ethylamino)-toluene; N-ethyl-N-β-hydroxyethyl-p-phenylene diamine; N,N-bis-(β-hydroxyethyl)-p-phenylene diamine or 2-amino-5-(N-ethyl-N-β-hydroxyethylamino)-toluene. Other suitable colour developers are described for example in J. Amer. Chem. Soc. 73, 3100 (1951).

The photographic material may contain the usual colour couplers which may be incorporated in the silver halide layers themselves. Examples of suitable colour couplers may be found in the article entitled "Farbkuppler (Colour Couplers)" by W. Pelz in "Mitteilungen aus den Forschungslaboratoren der Agfa, Leverkusen/Munchen", Vol III (1961), and in K Venkataraman's book entitled "The Chemistry of Synthetic Dyes", Vol 4, 341 to 387, Academic Press, 1971. Other suitable couplers are 2-equivalent couplers, for example the known DIR-couplers. The colour couplers may be added to the photosensitive silver halide emulsions or to other casting solutions by the usual methods.

Where the couplers are water-insoluble or alkali-insoluble compounds, they may be emulsified in known manner. So-called coupler solvents or oil formers may additionally be used for incorporating hydrophobic compounds such as these by emulsification as described for example in U.S. Pat. Nos. 2,322,027; 2,533,514; 3,689,271; 3,764,336 and 3,765,897.

Gelatin is preferably used as the binder for the photographic layers. However, it may be completely or partly replaced by other natural or synthetic binders.

The emulsions may also be chemically sensitised, for example by the addition during chemical ripening of sulphur-containing compounds, for example allyl isothiocyanate, allyl thiourea and sodium thiosulphate. Other suitable chemical sensitisers are reducing agents, for example the tin compounds described in Belgian Pat Nos. 493,464 or 568,687; polyamines such as diethylene triamine or aminomethyl sulphinic acid derivatives, for example according to Belgian Pat. No. 547,323. Other suitble chemical sensitisers are noble metals and noble metal compounds, such as gold, platinum, palladium, iridium, ruthenium, rhodium. The emulsions may also be sensitised with polyalkylene oxide derivatives, for example with polyethylene oxide having a molecular weight in the range from 1000 to 20,000, and with condensation products of alkylene oxides and alcohols, aliphatic carboxylic acids, aliphatic amines, aliphatic diamines and amides.

The emulsions may also be optically sensitised, for example with the usual polymethine dyes, such as neutrocyanines, basic or acid carbocyanines, rhodacyanines, hemicyanines, styryl dyes and oxonoles. Sensitisers such as these are described in F. M. Hamer's book entitled "The Cyanine Dyes and Related Compounds", (1964).

The layers of the photographic material may be hardened in the usual way, for example with formaldehyde or with halogen-substituted aldehydes containing a carboxyl group, such as mucobromic acid, diketones, methane sulphonic acid esters and dialdehydes. The photographic layers may also be hardened with epoxide, heterocyclic ethylene imine or acryloyl hardeners. It is also possible to harden the layers by the process according to German Offenlegungsschrift No. 2,218,009 in order to obtain colour photographic materials which are suitable for processing at high temperatures. The photographic layers or, rather, the colour photographic multilayer materials may also be hardened with diazine, triazine, or 1,2-dihydroquinoline hardeners. Examples of such hardeners are diazine derivatives containing alkyl or aryl sulphonyl groups, derivatives of hydrogenated diazines or triazines such as, for example, 1,3,5-hexahydrotriazine, fluorine-substituted diazine derivatives such as, for example, fluoropyrimidine and esters of disubstituted 1,2-dihydroquinoline- or 1,2-dihydroisoquinoline-N-carboxylic acids. Other suitable hardeners are vinyl sulphonic acid hardeners, carbodiimide or carbamoyl hardeners of the type described, for example, in German Offenlegungsschrifts Nos. 2,263,602; 2,225,230 and 1,808,685; French Pat. No. 1,491,807; German Pat. No. 872,153 and East German Pat. No. 7218. Other suitable hardeners are described, for example, in British Pat. No. 1,268,550.

The stabilisers according to the invention are preferably added to the photosensitive silver halide emulsions after chemical ripening. The stabilisers may of course also be added to other photographic layers. The concentration of the stabilisers in the emulsion may vary within wide limits and depends upon the type of emulsion and upon the required effect. In general, the required effects are obtained with quantities of from 20 mg to 2 g and, more particularly, with quantities of from 50 to 500 mg per mole of silver halide or per g of silver added to a layer containing colloidal silver, for example a silver filter yellow layer or black layer. The optimal addition for each emulsion may readily be determined by standard tests.

The invention is illustrated by the following Examples.

EXAMPLE 1

A highly sensitive silver iodobromide emulsion containing 5 mole percent of iodide and 0.5 mole of silver halide per kg of emulsion and having a silver (ex pressed as $AgNO_3$)/gelatin ratio of 1:1.3 was ripened with sulphur and gold compounds to obtain optimum sensitivity.

The emulsion was divided into several parts and the following substances were added per kg of emulsion:

| | |
|---|---|
| 4-hydroxy-6-methyl-1,3,3a,7-tetraazaindene 1% aqueous-alkaline solution | 150 mg |
| saponin, 10% solution in water | 600 mg |
| formaldehyde, 10% solution in water | 10 ml |

The substances according to the invention as listed in Table 3, dissolved in acetone and alcohol, were also added in the quantities indicated. The quantities were selected in such a way that sensitivity was still not significantly affected.

The emulsions were then cast onto a cellulose acetate substrate in a layer thickness corresponding to a silver coating of from 7.3 to 7.5 g of silver nitrate per square meter. A protective layer was then applied to the emulsion layer in a thickness corresponding to 2 g of gelatin per square meter.

The samples were subjected to a so-called fresh test and to a heating-cabinet test after storage for 3 days at 60° C.

The samples were then exposed behind a grey wedge in a sensitometer and developed for 16 minutes at 20° C. in a developer I having the following composition:

| Developer I | |
|---|---|
| ethylene diamine-N,N,N',N'—tetraacetic acid | 1.5 g |
| sodium hexametaphosphate | 1.0 g |
| sodium sulphite sicc. | 60 g |
| borax | 12 g |
| hydroquinone | 6 g |
| 1-phenyl-2-pyrazolidone | 0.7 g |
| potassium bromide | 3 g |
| made up with water to 1 liter. | |

This is followed by a stop bath consisting of 10 g of sodium acetate sicc. and 20 g of 96% glacial acetic acid in 1 liter of water. This is then followed by fixing with 15% ammonium thiosulphate solution and 1% sodium sulphite solution and then by rinsing. The results of the sensitometric evaluation are set out in Table 3.

TABLE 3

| Compound No. | mg/kg | Developer I | | | | | |
|---|---|---|---|---|---|---|---|
| | | Fresh test | | | Heating-cabinet test (3 days at 60° C.) | | |
| | | speed* | Γ | fogging | speed* | Γ | fogging |
| control sample | — | standard | 0.95 | 0.22 | standard | 1.07 | 0.24 |
| 1.24 | 130 | −0.3° | 0.97 | 0.15 | +0.3° | 0.92 | 0.16 |
| 1.12 | 123 | −0.2° | 0.95 | 0.15 | +0.5° | 0.91 | 0.15 |
| 1.1 | 116 | ±0 | 0.97 | 0.13 | +1.0° | 0.93 | 0.14 |
| 1.17 | 118 | +0.4° | 0.97 | 0.14 | +0.2° | 0.97 | 0.15 |
| 1.5 | 137 | −0.2° | 0.99 | 0.15 | ±0 | 0.93 | 0.16 |

*an increase of 3 units corresponds to a doubling of speed

The compounds according to the invention stabilise fogging, speed and gradation during storage.

EXAMPLE 2

26 mg of 4-hydroxy-6-methyl-1,3,3a,7-tetraazaindene in aqueous alkaline solution, 263 g of a 10% gelatin solution, 1200 g of a 4% coupler dispersion of the following yellow coupler:

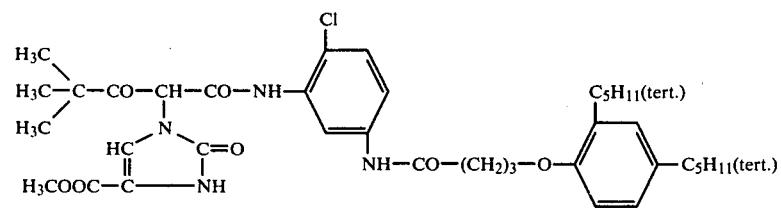

a wetting agent and 3200 ml of water were added to 1 kg of a blue-sensitised silver iodobromide emulsion containing 0.28 mole of silver halide (consisting of silver bromide with a content of 0.4 mole percent of silver iodide) and having a silver (expressed as silver nitrate)/gelatin ratio of 1:2. The pH-value was then adjusted to 6.8 and the emulsion thus obtained was divided into several equal parts and the compounds according to the invention as shown in Table 4 dissolved in acetone and alcohol, were added to the individual samples in the quantities indicated, which were selected so that sensitivity was affected as little as possible.

The emulsion samples were cast onto corona-irradiated polyethylene-coated paper in a layer thickness corresponding to a silver coating of 0.75 g of silver nitrate per square meter. A protective layer containing a suitable hardener and a wetting agent was applied to each emulsion layer in a layer thickness corresponding to 2 g of gelatin per square meter.

After drying and storage for 8 weeks under normal conditions, the materials were exposed behind a $^3\sqrt{2}$ step wedge and were developed for 210 seconds at 33° C. in developer II having the following composition.

| Developer II | |
|---|---|
| trisodium salt of nitrilo tri-acetic acid | 2 g |
| sodium sulphite sicc. | 1.8 g |
| potassium bromide | 0.6 g |
| potassium carbonate | 3.3 g |
| diethylene glycol | 18 ml |
| benzyl alcohol | 16 ml |
| hydroxyl amine sulphate | 3.7 g |
| 4-amino-'N—ethyl-N—β-methylsulphon-amidoethyl)-toluidine-3/2-sulphate monohydrate | 5.7 g |
| made up with water to 1 liter. | |

Further processing comprised the following baths:
Stop bath: buffer solution of sodium acetate and acetic acid adjusted to pH 6.5.
Bleach-fixing bath:
10 g of ethylene diamine-N,N,N',N'-tetraacetic acid, Na4-salt,
10 g of sodium sulphite sicc.,
40 g of sodium-iron(III)salt of ethylene diamine tetraacetic acid,
100 g of ammonium thiosulphate
made up with water to 1 liter and adjusted to pH 7.2 with sodium carbonate.

The processing times after development were as follows:

| Stop bath | 1 minute |
|---|---|
| rinsing | 1 minute |
| bleach-fixing | 2 minutes at 22° C. |
| rinsing | 3 minutes |

Yellow images of the step wedge were obtained. To determine "long-term fogging", unexposed samples were processed in the same way, except that they were developed for 300 seconds.

As the results set out in Table 4 show, the compounds reduce colour fogging, particularly in the event of prolonged development.

TABLE 4

| Compound No. | mg/kg | Speed* | Gradation | $D_{max}$ | Fogging | Long-term Fogging |
|---|---|---|---|---|---|---|
| control sample | — | 17.5 | 2.44 | 1.82 | 0.23 | 0.27 |
| 1.24 | 104 | 17.6 | 2.41 | 1.76 | 0.09 | 0.11 |
| 1.12 | 99 | 17.1 | 2.40 | 1.80 | 0.10 | 0.12 |
| 1.1 | 93 | 17.6 | 2.46 | 1.82 | 0.12 | 0.13 |
| 1.17 | 115 | 17.0 | 2.40 | 1.79 | 0.10 | 0.11 |
| 1.5 | 110 | 17.4 | 2.41 | 1.80 | 0.12 | 0.13 |

*speed = x step at density 1

EXAMPLE 3

The advantageous effect of the substances according to the invention becomes particularly clear when the photographic material is developed in the presence of sodium thiosulphate. In practice, development in the presence of thiosulphate occurs through the entrainment of developer substance into the fixing bath or into the bleach-fixing bath, particularly where processing is carried out at high speed without any stop bath between the developer and fixing or bleach-fixing bath, and through the entrainment of sodium thiosulphate into the developer, for example by clips and other parts of the apparatus used for processing. This gives rise to heavy fogging in standard photographic materials. If, by contrast, photographic material according to the invention is developed with the developer containing thiosulphate, fogging is drastically reduced, as shown in Table 5. The material corresponds to that indicated in Example 2.

| Developer III | |
|---|---|
| N—butyl-N—ω-sulphobutyl-p-phenylene diamine | 5 g |
| hydroxyl amine hydrochloride | 2.7 g |
| sodium sulphite sicc. | 3 g |
| trisodium salt of nitrilotriacetic acid | 2 g |
| potassium carbonate | 75 g |
| potassium bromide | 1 g |
| sodium thiosulphate | 1 g |
| made up with water to 1 liter. | |

Processing is carried out in the same way as in Example 2, except that unexposed material is developed for 2 minutes at 25° C. in developer III instead of developer II.

The results set out in Table 5 are obtained.

TABLE 5

| Compound No. | mg/kg | Fogging |
|---|---|---|
| control sample | — | 0.31 |
| 1.24 | 104 | 0.17 |
| 1.12 | 99 | 0.20 |
| 1.1 | 93 | 0.21 |
| 1.17 | 115 | 0.18 |
| 1.5 | 110 | 0.21 |

EXAMPLE 4

A colour photographic multilayer material A was prepared on a corona-irradiated polyethylene-coated paper substrate, containing a blue-sensitised layer, a green-sensitised layer and a red-sensitised layer and a gelatin separation layer between the respective emulsion layers. 85 mg of compound 1.24 (per mole of silver halide) and 72 mg of compound 1.24 (per mole of silver halide) in the form of a 0.1% solution in acetone/ethanol (1:1) were added respectively to the emulsions ready for casting for the blue-sensitised yellow layer and the green-sensitised magenta layer.

A corresponding colour photographic multilayer material B was prepared for comparison, the emulsions containing none of the compounds according to the invention. The materials A and B were exposed in a standard sensitometer behind a test image which contained a grey, a blue, a green and a red step wedge. The materials were then developed for 110 seconds at 35° C. in the following developer IV.

| Developer IV | |
|---|---|
| N—butyl-N—ω- sulphobutyl-p-phenylene diamine | 5 g |
| hydroxyl amine hydrochloride | 1.2 g |
| sodium sulphite (sicc.) | 2 g |
| sodium hexametaphosphate | 2 g |
| potassium carbonate | 75 g |
| potassium bromide | 1 g |
| made up with water to 1 liter. | |

Further processing comprised the following baths:

| Stop bath: | buffer solution of sodium acetate and acetic acid, pH 6.5. |
|---|---|
| Bleach fixing bath: | |
| sodium salt of ethylene diamine tetraacetic acid | 10 g |
| sodium sulphite (sicc.) | 2 g |
| sodium-iron(III)-salt of ethylene diamine tetraacetic acid | 40 g |
| disodium phosphate | 13 g |
| ammonium thiosulphate | 100 g |
| made up with water to 1 liter, pH 7.0. | |

The processing times after development were as follows:

| Stop bath | 1 minute |
|---|---|
| rinsing | 1 minute |
| bleach-fixing bath | 5 minutes |
| rinsing | 10 minutes |

Sensitometric evaluation showed that materials A and B had substantially the same sensitivity, gradation and maximum density.

In another test series, *unexposed* materials A and B were processed in the same way, except that 1 g of sodium thiosulphate per liter was added to developer IV.

The fog values shown in Table 6, as measured behind a blue filter, were obtained depending upon the development time.

TABLE 6

| Material | Time | | | |
|---|---|---|---|---|
| | 1.5 mins. | 2 mins. | 3 mins. | 4 mins. |
| A | 0.22 | 0.27 | 0.50 | 0.56 |
| B | 0.26 | 0.32 | 0.58 | 0.63 |

The material A according to the invention had a distinctly lower fogging level.

EXAMPLE 5

1.5 g of 4-hydroxy-6-methyl-1,3,3a,7-tetraazaindene in aqueous alkaline solution were added to 1 kg of a green-sensitised silver iodobromide emulsion having a silver (expressed as silver nitrate)/gelatin ratio of 1:0.4 and a silver halide content of 0.91 mole per kg of emulsion (5 mole percent of iodide). The emulsion thus obtained was divided into several equal parts and the compounds according to the invention as shown in the following Table, dissolved in acetone and alcohol were added to the individual samples in the quantities indicated. Before casting, the following substances were added per kg of emulsion: 75 g of a 5% gelatin solution, 109 g of an 11.1% coupler dispersion of the following magenta coupler

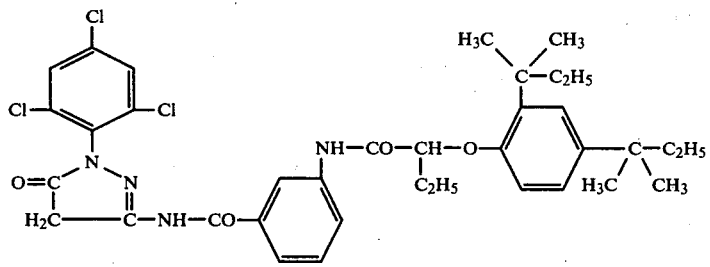

wetting agents in aqueous solution and 1180 ml of water. The emulsions were cast onto the antihalation layer, consisting of a silver dispersion, of a cellulose acetate substrate in a layer thickness corresponding to a silver coating of from 4.9 to 5.0 g of silver nitrate per square meter.

A protective layer containing a suitable hardener and a wetting agent was applied to each emulsion layer in a thickness corresponding to 2 g of gelatin per square meter.

The samples were subjected to a fresh test and to a heating-cabinet test for 3 days at 38° C./60% relative air humidity.

The samples were then exposed behind a step wedge in a sensitometer and developed for 3.75 minutes at 38° C. in the following developer V.

| Developer V | |
|---|---|
| 1-hydroxyethane-1,1-diphosphonic acid | 2 g |
| ethylene diamine-N,N,N',N'—tetraacetic acid | 2 g |
| potassium carbonate sicc. | 34.1 g |
| sodium hydrogen carbonate sicc. | 1.55 g |
| sodium disulphite sicc. | 0.28 g |
| sodium sulphite sicc. | 3.46 g |
| potassium bromide | 1.34 g |
| hydroxyl amine sulphate | 2.4 g |
| 4-amino-3-methyl-N—ethyl-N—($\beta$-hydroxyethyl)-aniline | 4.7 g |
| made up with water to 1 liter. | |

Further processing comprised the following baths:

| Stop bath | 1 minute at 38° C. |
|---|---|
| bleaching bath | 3.25 minutes at 38° C. |
| rinsing | 3.5 minutes at 38° C. |
| fixing bath | 3.25 minutes at 38° C. |
| rinsing | 5 minutes at 38° C. |

The stop, bleaching and fixing baths used correspond to those normally used (British Journal of Photography, 1974, pages 597 and 598).

Three known stabilisers containing mercapto groups A, B and C were used for comparison:
A = 5-mercapto-1-phenyl-tetrazole
B = 5-mercapto-1-(m-carboxyphenyl)-tetrazole (German Pat. No. 1,273,323 and U.S. Pat. No. 3,695,881):
C = p-[3-(2-mercapto-3,4-dihydro-4-ketoquinazolinyl)-benzene sulphonic acid. This compound is known as an anti-fogging agent from German Offenlegungsschrift No. 1,962,605.

The results obtained are shown in Table 7.

The comparison substances show a weaker antifogging effect, in addition to which B depresses sensitivity whilst A and C flatten gradation.

TABLE 7

| Compound No. | mg/kg | Fresh test speed* | $\gamma$ | fogging | Heating-cabinet test speed* | $\gamma$ | fogging |
|---|---|---|---|---|---|---|---|
| control sapmpe | — | 33.6 | 0.56 | 0.65 | 34.1 | 0.53 | 0.67 |
| 1.24 | 130 | 34.0 | 0.61 | 0.25 | 34.6 | 0.56 | 0.26 |
| 1.39 | 168 | 34.1 | 0.64 | 0.25 | 34.5 | 0.60 | 0.28 |
| 1.12 | 123 | 33.5 | 0.58 | 0.23 | 33.8 | 0.55 | 0.29 |
| 1.1 | 116 | 33.6 | 0.56 | 0.29 | 34.2 | 0.53 | 0.34 |
| 1.17 | 144 | 34.0 | 0.68 | 0.24 | 34.3 | 0.54 | 0.29 |
| 1.5 | 137 | 34.2 | 0.61 | 0.25 | 34.6 | 0.58 | 0.26 |
| A | 53 | 33.9 | 0.66 | 0.50 | 32.2 | 0.47 | 0.52 |
| B | 178 | 32.4 | 0.60 | 0.52 | 33.6 | 0.60 | 0.50 |
| C | 134 | 33.9 | 0.57 | 0.38 | 34.4 | 0.43 | 0.43 |

*An increase of 3 in the speed figure quoted corresponds to a doubling of speed.

EXAMPLE 6

A multilayer material is prepared, containing the following layers in the order indicated on the substrate (quantities per square meter):

Layer I: gelatin protective layer containing 1.2 g of gelatin

Layer II: red-sensitised silver bromide-iodide emulsion layer containing 2.5 g of Ag and 3.0 g of gelatin with couplers dispersed therein for producing a cyan image Layer III: gelatin intermediate layer containing 1.2 g of gelatin Layer IV: green-sensitised silver bromide iodide emulsion layer containing 3.0 g of Ag and 3.3 g of gelatin with couplers dispersed therein for producing a magenta image Layer V: see Table 8

Layer VI: see Table 8

Layer VII: blue-sensitive silver bromide iodide emulsion layer containing 0.95 g of Ag and 1.7 g of gelatin with a coupler dispersed therein for producing a yellow image Layer VIII: protective layer containing a suitable hardener and a wetting agent and 1 g of gelatin The following individual materials were prepared from this material:
Material A:
  layer V: 1.2 g of gelatin layer VI: 1.0 g of gelatin and, contained therein, colloidal silver filter yellow having a colour density of 0.7.

Material B:
  layer V: as in material A
  layer VI: as in material A, but additionally containing 0.026 g of compound 1.24

Material C:
  layer V: as in material A
  layer VI: as in material A, but additionally containing 0.013 g of compound 1.17

Material D:
  layer V: as in material A, but additionally containing 0.042 g of compound 1.24
  layer VI: as in material A Material E:
  layer V: as in material A, but additionally containing 0.012 g of compound 1.17
  layer VI: as in material A.

After exposure behind a grey wedge, materials A to E are subjected to standard colour negative processing as described in Example 5.

Table 8 below shows the advantageous properties of materials B to E according to the invention in relation to comparison material A.

TABLE 8

| Material | $S_{pp}$ | $E_{relpp}$ | $S_{gb}$ | $E_{relgb}$ |
|---|---|---|---|---|
| A | 0.86 | 34.4 | 0.99 | 37.7 |
| B | 0.65 | 34.5 | 0.65 | 36.8 |
| C | 0.76 | 35.0 | 0.83 | 36.9 |
| D | 0.62 | 34.4 | 0.67 | 36.6 |
| E | 0.66 | 34.6 | 0.74 | 36.8 |

S: fogging
E: sensitivity
pp: magenta
gb: yellow

It is claimed:

1. A photographic material comprising a support layer and, applied thereto, at least one light sensitive silver halide emulsion layer and, optionally, further layers, wherein at least one layer contains a compound corresponding to formula (I) below:

<chemical structure> (I)

in which
  R represents alkyl, alkenyl, aryl, aralkyl or cycloalkyl;
  $R^1$, $R^2$ and $R^3$ which may be the same or different, represent hydrogen, alkyl, aryl, cycloalkyl or aralkyl;
  $R^4$ represents hydrogen or $-COR^5$;
  $R^5$ represents alkyl, aryl, cycloalkyl, aralkyl or $-OR^6$ and
  $R^6$ represents alkyl, aryl, cycloalkyl or aralkyl said compound being present in an amount sufficient to stabilize said photographic material against fogging.

2. A material as claimed in claim 1, wherein
  R represents alkyl or alkenyl containing from 1 to 6 carbon atoms; phenyl; or aralkyl containing at most 10 carbon atoms,
  $R^1$, $R^2$ and $R^3$ which may be the same or different and represent hydrogen, alkyl containing from 1 to 4 carbon atoms or phenyl,
  $R^4$ represents hydrogen or $-COR^5$,
  $R^5$ represents alkyl containing from 1 to 3 carbon atoms or a $C_1$-$C_6$-alkoxy or cycloalkoxy radical.

3. A material as claimed in claim 1, wherein in addition to a light sensitive silver halide emulsion layer, it contains a layer containing colloidal silver.

4. A material as claimed in claim 1, wherein compound I is present in a quantity of from 20 mg to 2 g per mole of silver halide.

5. A material as claimed in claim 3, wherein compound I is present in the layer containing the colloidal silver in a quantity of from 20 mg to 2 g per kg of silver.

6. A material as claimed in claim 1, wherein the material contains colour couplers.

7. A process for color developing a photographic material containing at least one supported light sensitive silver halide emulsion layer, wherein the color development is carried out in the presence of a compound corresponding to formula I below:

<chemical structure> (I)

in which
  R represents alkyl, alkenyl, aryl, aralkyl or cycloalkyl;
  $R^1$, $R^2$ and $R^3$ which may be the same or different, represent hydrogen, alkyl, aryl, cycloalkyl or aralkyl;
  $R^4$ represents hydrogen or $-COR^5$;
  $R^5$ represents alkyl, aryl, cycloalkyl, aralkyl or $-OR^6$ and
  $R^6$ represents alkyl, aryl, cycloalkyl, aralkyl said compound being present in an amount sufficient to stabilize said photographic material against fogging.

* * * * *